United States Patent
Epstein et al.

[11] Patent Number: 6,031,374
[45] Date of Patent: Feb. 29, 2000

[54] METHOD FOR EXTRACTING DEFORMATIONS FROM VELOCITY-ENCODED MAGNETIC RESONANCE IMAGES OF THE HEART

[76] Inventors: Frederick H. Epstein, 8212 Fountain Valley Dr., Gaithersburg, Md. 20879; Andrew E. Arai, 4003 Hampden St., Kensington, Md. 20895; Carl C. Gaither, 11698 South Laurel Dr., Laurel, Md. 20708; Steven D. Wolff, 7500 Woodmont Ave., Bethesda, Md. 20814

[21] Appl. No.: 08/937,725

[22] Filed: Sep. 25, 1997

Related U.S. Application Data

[60] Provisional application No. 60/043,890, Apr. 11, 1997.

[51] Int. Cl.[7] ............................................. G01V 3/00
[52] U.S. Cl. ................................... 324/306; 324/309
[58] Field of Search ............................. 324/306, 309, 324/307; 128/653.2

[56] References Cited

U.S. PATENT DOCUMENTS

| | | | |
|---|---|---|---|
| 5,408,180 | 4/1995 | Mistretta | 324/306 |
| 5,592,085 | 1/1997 | Ehman | 324/309 |
| 5,680,862 | 10/1997 | Song et al. | 128/653.2 |
| 5,825,186 | 10/1998 | Ehman | 324/309 |

OTHER PUBLICATIONS

*Phase Contrast Cine Magnetic Resonance Imaging,* Magnetic Resonance Quarterly, vol. 7, No. 4, pp. 229–254, Pelc, et al.

*Evaluation of Myocardial Motion Tracking With Cine–Phase Contrast Magnetic Resonance Imaging,* Investigative Radiology, vol. 29, No. 12, 1038–1042, 1994, Pelc, et al.

*Magnetic Resonance Imaging of Myocardial Kinematics, Techniques to Detect, Localize and Quantify the Strain Rates of the Active Human Myocardium,* Magnetic Resonance in Medicine 27, 52–67, 1992, Van J. Weeden.

*Myocardial Strain Mapping Using Phase Contrast Magnetic Resonance Imaging,* SMRM Abstracts 1992, McKinnon, et al.

*Validation of Cine Phase–Contrast MR Imaging for Motion Analysis,* JMRI 1995; 5:331–338, Lingammneni, et al.

*Primary Examiner*—Christine K. Oda
*Assistant Examiner*—Tiffany A. Fetzner
*Attorney, Agent, or Firm*—Barry E. Sammons; Christian G. Cabou

[57] ABSTRACT

An MRI scan is conducted in which velocity encoded NMR data is acquired for a slice through the heart. Velocity images and magnitude images are reconstructed at multiple cardiac phases and masks are formed using the magnitude images. The masks are applied to the velocity images to isolate the left ventricle, and rigid body motion is calculated and subtracted from the masked velocity images to indicate deformation of the left ventricle.

12 Claims, 4 Drawing Sheets

METHOD FOR EXTRACTING DEFORMATIONS FROM VELOCITY-ENCODED MAGNETIC RESONANCE IMAGES OF THE HEART

RELATED APPLICATIONS

This application is based on Provisional Application No. 60/043,890 filed on Apr. 11, 1997.

BACKGROUND OF THE INVENTION

The field of the invention is nuclear magnetic resonance imaging methods and systems.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Most NMR scans currently used to produce medical images require many minutes to acquire the necessary data. The reduction of this scan time is an important consideration since reduced scan time increases patient throughput, improves patient comfort, and improves image quality by reducing motion artifacts. There is a class of pulse sequences which have a very short repetition time (TR) and result in complete scans which can be conducted in seconds rather than minutes. When applied to cardiac imaging, for example, a complete scan from which a series of images showing the heart at different phases of its cycle can be acquired in a single breath-hold.

The prognosis of patients with a wide variety of cardiac diseases (including coronary artery disease, valvular heart disease, congestive heart failure and cardiac arrhythmias) has been closely linked to the degree of left ventricular ejection fraction a quantitative measure of global ventricular function. Quantitative measures of regional contractile function could have significant prognostic and therapeutic importance. For example, many patients with severe coronary artery disease may have normal regional and global left ventricular function at rest but have abnormalities induced by stress. In clinical practice, patients with coronary artery disease can be detected by stress echocardiography based on new functional deficits during stress. However, interobserver variability of this type of qualitative measure is an inherent limitation that could be improved with quantitative measures. Thus, there is a need for high quality quantitative measures of regional cardiac function.

Invasive measurements of regional contractile function based on ventriculography are limited by arrhythmias induced by the injection, the failure to visualize the myocardium directly, and the consequent limited ability to differentiate endocardial motion due to regional contraction from endocardial motion due solely to tethering. The latter arguments also apply to noninvasive ventriculographic measures of contractile function such as radionuclide ventriculography and echocardiographic analysis of endocardial motion. Regional wall thickening by echocardiography, CT, or MRI is a better measure of regional function but image resolution and irregular myocardial contours limit quantitation. These methods are also susceptible to through plane motion and thus do not image the same myocardium throughout the cardiac cycle. Echocardiography windows and poor endocardial definition, particularly after surgery, cause further compromise. Regional wall thickening using gated SPECT Tc-sestamibi has the appeal of both perfusion and contraction in the same exam. It remains to be seen, however, whether the relatively low image resolution and further degradation due to respiratory motion can be overcome in this prior method to produce quantifiable measures of regional contractile function that have clinical use.

MRI has been used to quantify regional myocardial function using two distinct methodologies: tagging; and velocity encoded phase contrast. Both methods can noninvasively assess specific parts of the myocardium and are inherently quantifiable. While myocardial tagging techniques such as that proposed by Axel L. Dougherty L: "MR Imaging Of Motion With Spatial Modulation Of Magnetization," Radiology 1989; 171:841–845; and Zerhouni E A, Parish D M, Rogers W J, Yang A, Shapiro E P: Human Heart: "Tagging With MR Imaging—A Method for Noninvasive Assessment of Myocardial Motion," Radiology 1988; 169:59–63, have received considerable attention in recent years, the tag spacing must be several times larger than the image resolution to allow accurate localization. Within the limits set by tag spacing, the deformations of the tags theoretically can be quantified with a spatial accuracy significantly better than the image resolution. Finite element analysis of myocardial tags has been used to quantify regional myocardial mechanics in a variety of heart diseases.

Velocity encoded phase contrast MRI can be used as described by Pelc N J, Drangova M, Pelc L R, Zhu Y, Noll D C, Bowman B S, Herfkens R J: "Tracking Of Cyclic Motion With Phase-Contrast Cine MR Velocity Data," J. Magn Reson Imaging 1995; 5:339–345; Pelc L R, Sayre J, Yun K, Castro L J, Herfkens R J, Miller D C, Pelc N J: "Evaluation Of Myocardial Motion Tracking With Cine-Phase Contrast Magnetic, Resonance Imaging," Invest Radiol 1994; 29:1038–1042; and Wedeen V J: "Magnetic Resonance Imaging of Myocardial Kinematics, Technique to Detect, Localize, and Quantify The Strain Rates Of The Active Human Myocardium," Magn Reson Med 1992; 27:52–67, to track the position of a voxel of myocardium across the cardiac cycle based on its velocity and acceleration as a function of time. To date however, motion tracking methods are sensitive to accumulated errors that can result in position errors of 1–2 pixels. Alternatively, phase contrast velocity data can be analyzed in strict mechanical terms as the strain rate. Strain rate analysis uses the three or four nearest neighbor velocity determinations to correct for local translation and rotation on a pixel-by-pixel basis with final estimation of the major and minor axes of regional deformation. Since normal myocardial deformation is primarily radially oriented, the major axis of strain rate is roughly equivalent to the time derivative of wall thickening/thinning. Strain rate analysis as implemented thus far requires multiple differential calculations and thus is susceptible to noise. It also is sensitive to partial volume problems since it requires information from surrounding pixels.

The basic premise of all these MRI methods has been that gross motion of the heart through the chest should be eliminated to reveal the deformation associated with heart contractile function. However, the MRI system measures the spin motions relative to the stationary reference of the MRI system. As a result, velocities acquired from the myocardium are a combination of 3-dimensional rotation, translation, and deformation of the heart coordinated with the cardiac cycle. Respiratory motion contributes additional rotations and translations through the chest. Abnormal contractile patterns such as bundle branch block further complicate the interpretation of myocardial velocities from the external stationary frame of reference. Thus, a number of parameters modify the velocity of a region of the heart relative to an external reference point on the MRI system.

SUMMARY OF THE INVENTION

The present invention is a method for acquiring velocity images of a moving organ such as the heart and extracting the contractile motion from the velocity data. More particularly, an MRI phase difference image is acquired using a pulse sequence that includes a velocity-encoding gradient; rigid body motion of a selected region of interest in the image is calculated, and the rigid body motion is subtracted from the image to yield an image containing primarily deformation velocities of the organ.

A general object of the invention is to provide an image which indicates quantitatively the contractile motion of the heart. All velocity information in the image pixels is used to calculate the bulk, net translation and rotation of the heart relative to the MRI system reference. By subtracting these motions, a conversion from the fixed frame of reference of the MRI scanner to a moving frame of reference located at the center of the heart is accomplished. Residual velocity information reveals the desired deformations of the heart.

GENERAL DESCRIPTION OF THE INVENTION

Figure 1:
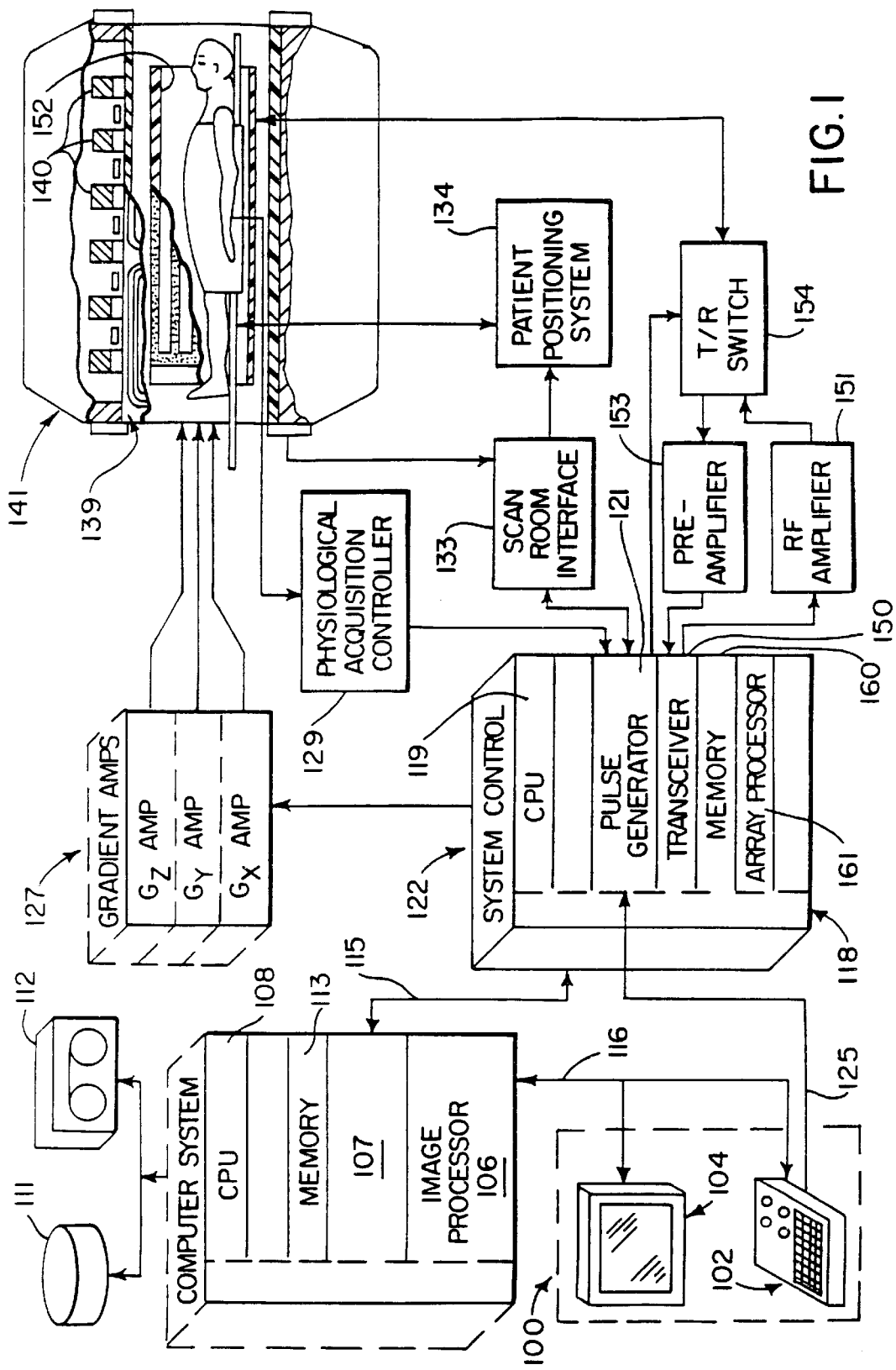
FIG. 1 is a block diagram of a known MRI system which is modified to employ the present invention.

Two sets of velocity-encoded images are acquired with the velocity-encoding applied in two orthogonal in-plane directions as a function of cardiac cycle.

Magnitude images that correspond temporally to the velocity encoded images are also acquired. The magnitude images are used to generate masks of the left ventricle ("LV"). The center of each slice is determined by computing the centroid of the LV masks.

$$x_{centroid} = \frac{m_{10}}{m_{00}} \quad y_{centroid} = \frac{m_{01}}{m_{00}} \quad (1)$$

Here $m_{ij}$ are the spatial moments of the LV mask and are defined by $$m_{ij} = \sum_x \sum_y x^i y^j a_{xy} \quad (2)$$

where i+j is the order of the moment, x and y are the pixel coordinates relative to some arbitrary origin and $a_{xy}$ is the value of the mask at the point x,y (1 if the point is in the mask and 0 otherwise).

Any rigid body motion of the heart can be transformed into a rotation (in three dimensions) about the centroid of the slice and a translation of the centroid. The velocities due to a rotation of the heart at any time t around the centroid with angular velocity $\bar{\omega}=\omega_x\hat{x}+\omega_y\hat{y}+\omega_z\hat{z}$ is given by $\bar{v}=\omega_i\times\bar{r}$ where $\omega_i$ is the constant angular velocity about the i-axis at time t. The angular velocity is a function of time in the heart, but during the short interval during which velocity encoding occurs, $\omega_i$ may be considered constant. The resultant Cartesian velocities in the plane of the slice are thus given by $$v_x = z\omega_y - y\omega_z$$
$$v_y = x\omega_z - z\omega_x \quad (3)$$

Here, x,y and z are measured relative to the centroid of the LV mask. Through-plane velocities ($v_z$) are not considered here. However, they could be considered if a 3-D data set were acquired and a long-axis analysis was performed. Translation velocities of the heart simply add to $v_x$ and $v_y$. A portion of these translational velocities are due to apparent translations of the centroid of the slice due to off-center rotations.

The velocity encoded measurements include the aggregate effects of rigid body translations, rotations and deformations in the imaging plane due to the contraction and relaxation of the LV. Thus, the x and y velocities measured are given by $$v_x = z\omega_y - y\omega_z + v_{x\ translation} + v_{x\ deformation}(x,y)$$
$$v_y = x\omega_z - z\omega_x + v_{y\ translation} + v_{y\ deformation}(x,y) \quad (4)$$

In order to assess cardiac function, $\bar{v}_{deformation} = v_{z\ deformation}(x,y)\hat{x} + v_{y\ deformation}(x,y)\hat{y}$ is required.

For measurements in a given slice, z is a constant. Since $\bar{\omega}$ and the translational velocities are considered constant during the velocity encoding interval, $v_x$ and $v_y$ reduce to the form $$v_x = A_1 - y\omega_z + v_{x\ deformation}(x,y)$$
$$v_y = A_2 + x\omega_z + v_{y\ deformation}(x,y) \quad (5)$$

where $A_1$ and $A_2$ are constants.

Figure 5:
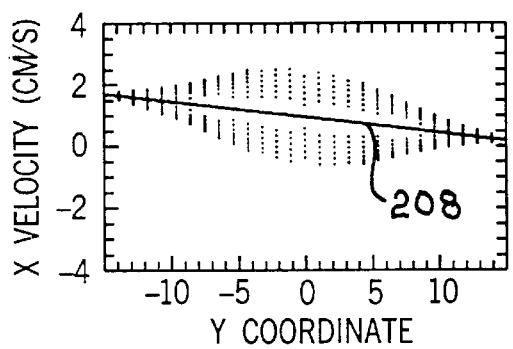
FIGS. 5–8 are graphic representations of a simulated heart undergoing bulk motion in addition to deformation.
Figure 6:
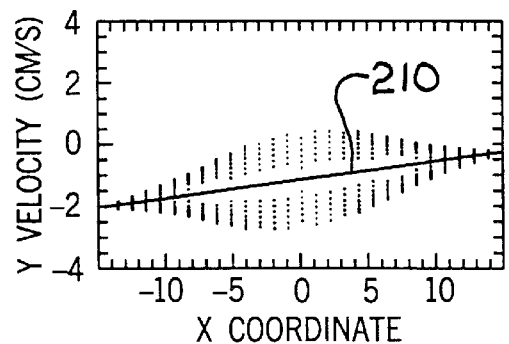
Figure 7:
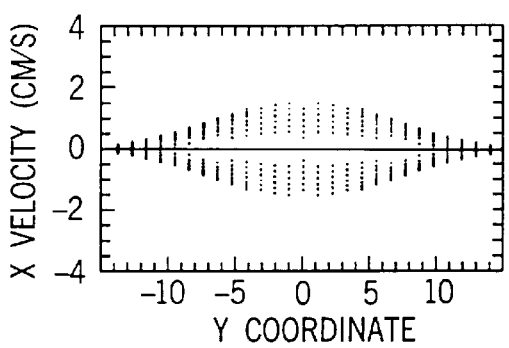
Figure 8:
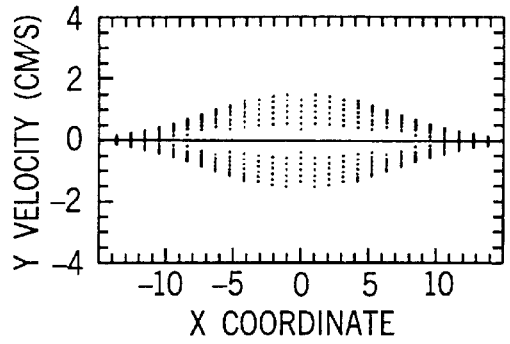
Figure 9:
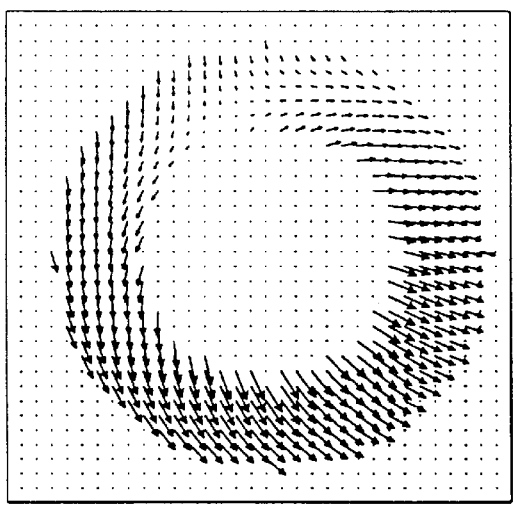
FIGS. 9 and 10 are graphic representations showing the velocities in a slice through the simulated heart.
Figure 10:
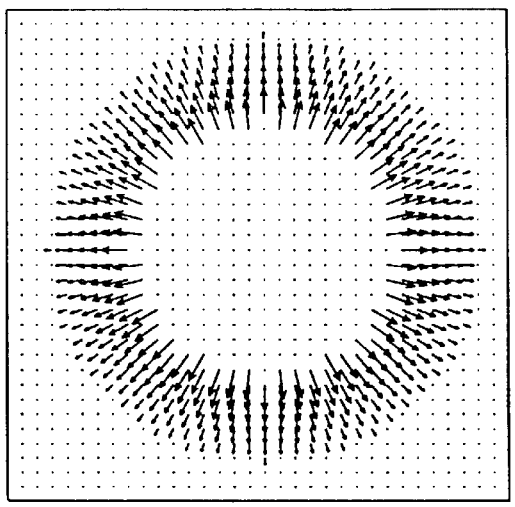

The effects due to translation and rotations can be determined by performing linear fits to $v_x$ as a function of y and to $v_y$ as a function of x. Note that if $\bar{v}_{deformation}\neq 0$, $v_x(y)$ and $v_y(x)$ are not necessarily single valued functions. FIGS. 5–8 show $v_x$ versus y and $v_y$ versus x for a simulated short axis slice of the heart undergoing rotational and translational rigid body motions in addition to a radial deformation. This deformation is characterized by a spatial velocity gradient of the radially directed velocities. In this simulation, $v_{x\ translation}$=1 cm/s, $v_{y\ translation}$=0.25 cm/s, $\omega_x$=0.1 radian/s, $\omega_y$=0.3 radian/s, $\omega_x$=0.5 radian/s. These values are not meant to be indicative of actual velocities in the heart but rather serve to illustrate the bull motion correction process. Observe that FIGS. 5 and 6 are not single valued functions. The dots represent the simulated velocity values while the line is the best linear fit to the data. The sign difference between the slopes in FIGS. 5 and 6 is predicted by equation 5. This line is due to the rigid body motions of the short axis slice and can now be subtracted from the raw velocity data. FIGS. 7 and 8 show the results of this subtraction, which reveal residual deformations of the slice. FIGS. 9 and 10 display the velocities in the velocity slice as vectors pointing in the velocity direction with magnitudes represented by the length of the vector: in FIG. 9 prior to correcting for bulk motion; and in FIG. 10 after correcting for bulk motion.

DESCRIPTION OF THE PREFERRED EMBODIMENT

Referring first to FIG. 1, there is shown the major components of a preferred magnetic resonance imaging (MRI) system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane 118. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scar. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

For a more detailed description of the transceiver 150, reference is made to U.S. Pat. Nos. 4,952,877 and 4,922,736 which are incorporated herein by reference.

Figure 2:
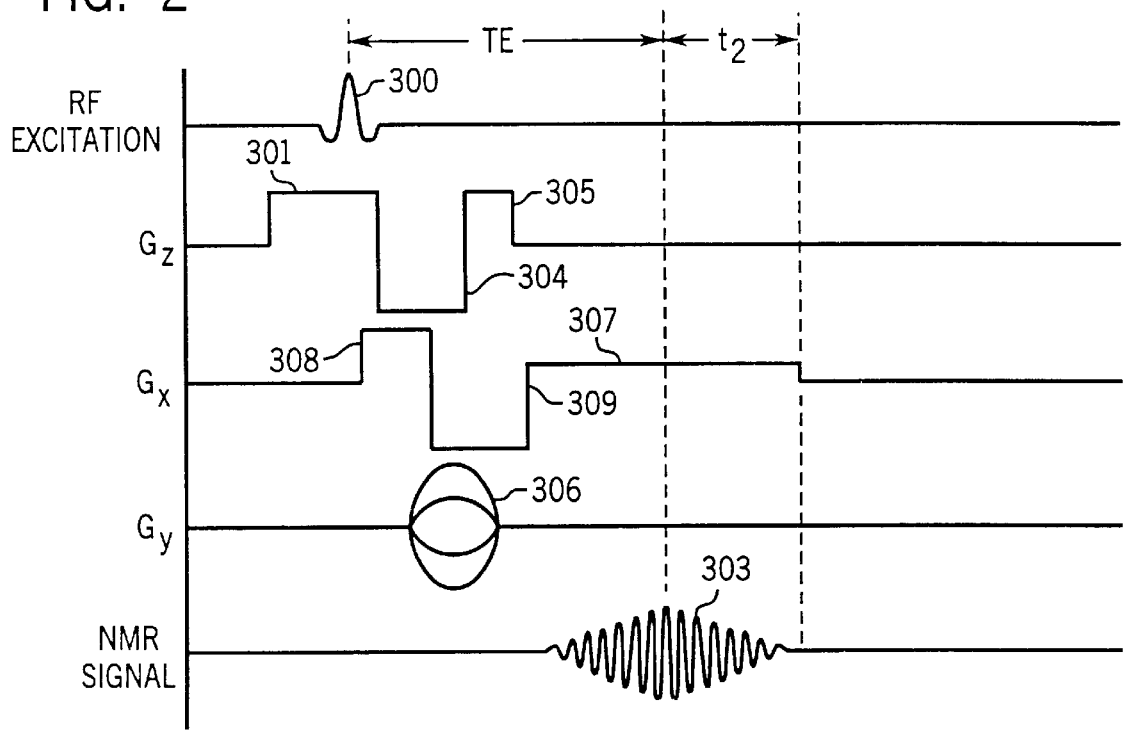
FIG. 2 is a graphic representation of a known pulse sequence which is adapted for use in practicing the preferred embodiment of the present invention.

The MRI system of FIG. 1 performs a series of pulse sequences to collect sufficient NMR data to reconstruct the desired velocity image. Referring particularly to FIG. 2, the first pulse sequence employs a selective RF excitation pulse 300 which is applied to the subject in the presence of a $G_z$ slice select gradient pulse 301. The excitation pulse 300 has a flip angle of α, with a preferred value of 15°. To compensate the NMR signal 303 which is produced at a time TE after the excitation pulse 300 for the phase shifts caused by the slice select gradient pulse 301 and to desensitize the NMR signal 303 to velocity along the z-axis, a negative $G_z$ gradient pulse 304 followed by a positive $G_z$ gradient pulse 305 are produced by the $G_z$ gradient coils as taught in U.S. Pat. No. 4,731,583. For example, one solution is to use a pulse 304 of the same width but opposite sign as the pulse 301 and the pulse 305 is one half the width and the same height as pulse 301. While the pulses 304 and 305 compensate for velocity along the z-axis, more complex gradient waveforms are also well known to those skilled in the art for compensating acceleration and even higher orders of motion.

To position encode the NMR signal 303 a phase encoding $G_y$ gradient pulse 306 is applied to the subject shortly after the application of the RF excitation pulse 300. As is well known in the art, a complete scan is comprised of a series of these pulses sequences in which the value of the $G_y$ phase encoding pulse is stepped through a series of, for example, 256 discrete phase encoding values to localize the position of the spins producing the NMR signal along the y-axis. Position along the x-axis is located by a $G_x$ gradient pulse 307 which is produced as the NMR gradient echo signal 303 is acquired and which frequency encodes the NMR signal 303. Unlike the $G_y$ phase encoding gradient pulse 306, the $G_x$ readout gradient pulse 307 remains at a constant value during the entire scan. To produce the gradient echo 303 and to desensitize it to velocity along the x direction, gradient pulses 308 and 309 precede the gradient pulse 307 as taught in U.S. Pat. No. 4,731,583.

The NMR signal 303 is acquired by the system transceiver 122 and digitized into a row of 256 complex numbers which are stored in the memory of the main computer 101. For each value of the $G_y$ phase encoding gradient an NMR signal 303 is produced, acquired, digitized and stored in a separate row of 256 complex numbers. At the completion of the scan, therefore, a two-dimensional (256×256) matrix of complex numbers is stored in the computer 101. These NMR signals which are produced when no flow sensitizing gradients are applied may be Fourier transformed into a conventional NMR image. The image data produced from these flow compensated signals is referred to herein as the reference image data.

Figure 3:
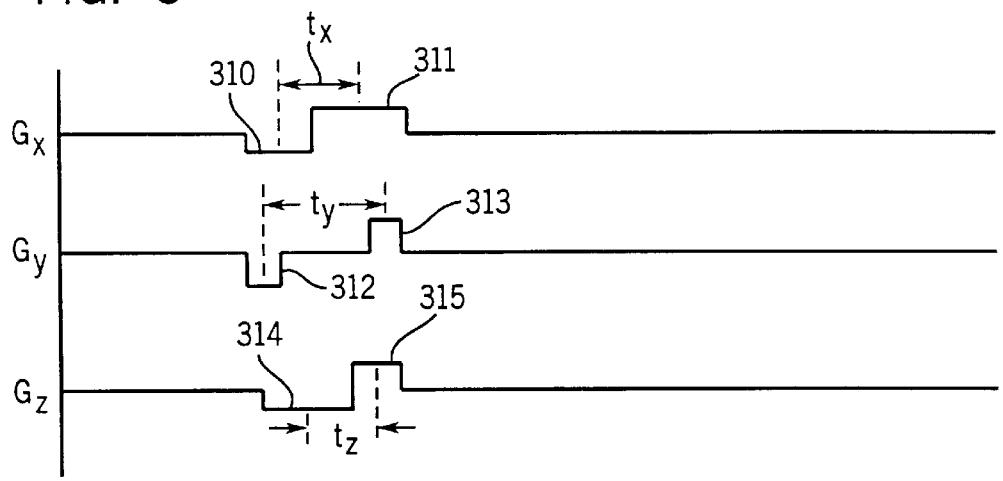
FIG. 3 is a graphic representation of the flow encoding gradients added to the pulse sequence of FIG. 2 to practice the preferred embodiment of the invention.

Two additional measurement cycles are conducted to acquire the data needed to practice the present invention. These measurement cycles employ the pulse sequence of FIG. 2 with one important difference—they include motion encoding magnetic field gradients which sensitize the NMR signal 303 to velocity along two perpendicular, in-plane axes. These motion encoding field gradients are produced by the same coils that produce the position encoding gradients $G_x$, $G_y$, and $G_z$ in the pulse sequence of FIG. 2. For the simple case of axial scans in which the image plane is perpendicular to the z-axis, one measurement is made with motion encoding along the x-axis and the second measurement is made with motion encoding along the y-axis. In the more general case where the image is oriented in an oblique plane, the two motion encoding measurements are made by applying a combination of gradients as will now be described with reference to FIG. 3.

After the reference measurement is made using the pulse sequence of FIG. 2, a motion encoding measurement may be made with the additional gradient pulses 310–315 shown in FIG. 3b. These additional gradient pulses 310–315 are added to the motion compensated gradient pulses of FIG. 2 and they produce gradients along the respective x, y and z axes which are bipolar. These bipolar gradient pulses 310/311, 312/313, and 314/315 sensitize the subsequent NMR signal 303 to velocity of spins moving along the x, y and z axes. The area, $A_x$, of each pulse 310 and 311 is the same and they are spaced apart by a time $t_x$. The change in the first moment is, therefore, $\Delta Mx_1 = A_x t_x$. Similarly, pulses 312 and 313 each having an area $A_y$, are spaced apart by time $t_y$, and produce a first moment change $\Delta Mx_1 = A_y t_y$. Pulses 314 and 315 have equal areas $A_z$ and are spaced apart by a time $t_z$. They produce a change in first moment $\Delta Mz_1 = A_z t_z$. As discussed previously, these first moment changes $\Delta Mx_1$, $\Delta My_1$ and $\Delta Mz_1$ determine the velocity sensitivity, which is typically controlled by adjusting the areas $A_x$, $A_y$ and $A_z$ respectively.

It should be apparent to those skilled in the art that many other pulse sequences can be used to acquire the necessary data. Also, there are many different ways to produce the motion encoding gradients for each measurement. For example, the gradient pulses can be shaped differently than those shown in FIG. 3, or they may be more separated in time to increase the first moment, or they may be more compact in their temporal duration. Also, spin echo sequences using a 180° RF pulse may be used, and rather than using bipolar gradient pulses, both velocity encoded pulses may have the same polarity if they are produced on opposite sides of the 180° RF pulse.

The flow encoded pulse sequence is employed in a prospectively cardiac gated, segmented scan of a slice through the heart. One view is obtained per segment, with one reference acquisition and one, in-plane, orthogonal flow encoded acquisitions in each segment. The segment is acquired with respect to the ECG gating signal to capture the heart at multiple cardiac phases across the cardiac cycle. A flip angle of 15°, TR of 21 ms, TE of 6.7 ms and a field of view of 33 cm is preferred. The velocity encoding first moment ranges from 10–15 cm/s. A Hadamard RF pulse is used to saturate spin magnetization on both sides of the image plane, and these saturation bands are located 12 mm from the image plane and have a width of 40 mm.

The flow encoded data and the reference data acquired during the scans are employed to produce two velocity images and a magnitude image. The velocity images are produced in the well-known manner by calculating the phase at each pixel of the two flow-encoding images and then subtracting the phase at each corresponding pixel. The magnitude image is produced from the reference image in the usual manner by calculating the square root of th sum of the squares of the complex values at each image pixel.

Figure 4:
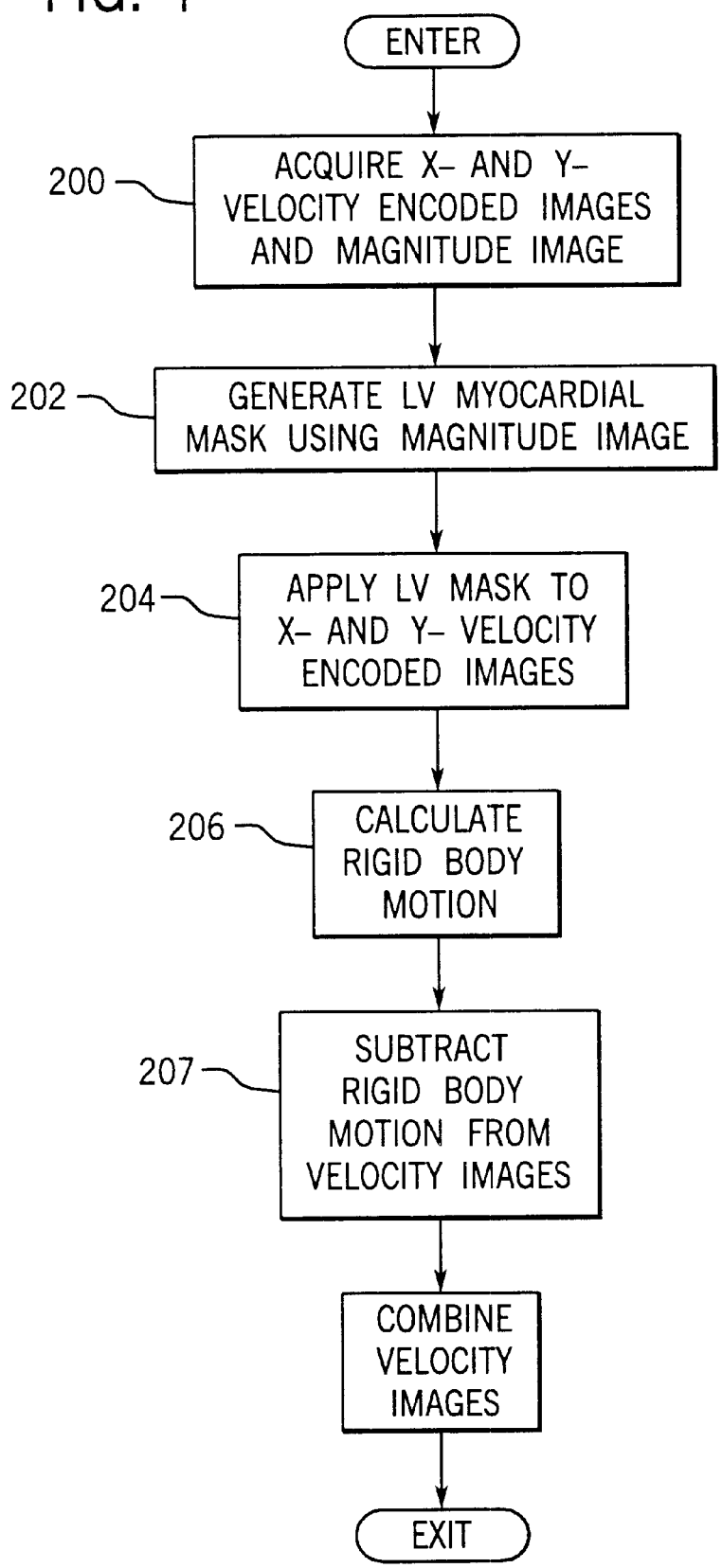
FIG. 4 is a flow chart of the steps performed by the MRI system of FIG. 1 to carry out the preferred embodiment of the invention.

Referring particularly to FIG. 4, the preferred method for practicing the present invention begins by acquiring and reconstructing the above-described velocity images and magnitude image, as indicated at process block 200. In the embodiment described short-axis images of the heart are produced and velocity encoding is performed along the x and y axes. Using the magnitude image, the next step indicated at process block 202 is to produce a mask of the left ventricle. This is accomplished by applying a threshold test to each magnitude image pixel. If the magnitude is greater than the threshold, the corresponding pixel in the mask is set to "1" and if it is not, the pixel is set to "0". Manual editing of the resulting mask may also be used to improve its quality.

The next step as indicated at process block 204 is to apply the mask to the two velocity images. Those image pixels in the velocity images which correspond to mask pixels set to "0" are also set to zero. The resulting masked velocity images indicate the velocities $v_x$ and $v_y$ at pixel locations in the left ventricle myocardium. If these images are combined into a single image where the velocity of each pixel is indicated by a vector, the image would appear as in FIG. 9. This image contains velocity components due to translational motion of the heart, rotation of the heart and contractile motion of the heart.

As indicated by process blocks 206 and 207, the next step is to calculate the rigid body motion components in the masked velocity images and subtract these components. Using the mask image the center of mass of the imaged left ventricle is calculated as indicated by the above equations (1) and (2).

The next step is to compensate for rigid-body motion. If the velocity values in the $v_x$ image are plotted as a function of their y coordinate, as measured from the center of mass, a distribution of values indicated in FIG. 5 is produced. If a line 208 is best fit to these values, the slope of the line 208 indicates angular rotation $\omega_z$ about the z-axis and the intercept of this line indicates rigid body translation and through-plane rotation $A_1$ as defined in equations 4 and 5. The same plot of the $v_y$ velocity values as a function of their location along the x-axis as measured from the center of mass provides the same information. As shown in FIG. 6, a line 210 is fit to these values and its slope indicates $-\omega_z$ and its intercept indicates $A_2$ in equations 4 and 5. Using the average of the two calculated angular velocities $\omega_z$ and the $A_1$ and $A_2$ values, the $-v_{x\ deformation}$ and $-v_{y\ deformation}$ images are calculated using equation (5). Plots of these two deformation velocity images are shown in FIGS. 7 and 8.

The last step is to combine the two deformation velocity images $v_{x\ deformation}$ and $v_{y\ deformation}$. This is a vector addition of the two images which preserve the magnitude and direction of the resulting deformation velocity $v_{deformation}$ at each image pixel. An exemplary display of the deformation velocity image is shown in FIG. 10 where it can be compared to the total velocity image in FIG. 9.

Processing myocardial MR velocity data according to the present invention essentially transforms the velocity information from the magnet frame of reference to the heart frame of reference. Many external factors contributing to gross motion of the heart are eliminated allowing the direct assessment of regional myocardial function. This type of quantitative regional function can be used in a wide range of clinical problems including but not limited to the following:

1). Assessment of systolic regional function in patients with coronary artery disease (CAD).

2). Detection of CAD during stress testing.

3). Assessment of regional diastolic function in patients with CAD.

4). Assessment of response to therapy such as angioplasty, coronary artery bypass surgery, thrombolytic therapy, or other medical therapy.

5). Detection of abnormal patterns of electrical activation including but not limited to the Wolff-Parkinson-White syndrome, other forms of block, and other abnormal activation patterns.

6). Assessment and optimization of mechanical activation patterns associated with pacemaker therapy.

7). Assessment of regional myocardial function in patients with cardiomyopathies including but not limited to hypertrophic cardiomyopathy, hypertrophic obstructive cardiomyopathy, restrictive cardiomyopathy, constrictive cardiomyopathy, dilated cardiomyopathy, trypanosomiasis.

8). Prediction of left ventricular remodeling after myocardial infarction.

9). Differentiation of infarction from hibernating or stunned myocardium.

10). Follow up of patients after cardiac transplantation for possible detection of tissue rejection.

11). Optimization of therapy for congestive heart failure.

We claim:

1. A method for producing an image with a magnetic resonance imaging system which indicates the deformation of a moving organ, the steps comprising:

a) acquiring velocity image data of the organ with the magnetic resonance imaging system using a pulse sequence which employs a velocity encoding gradient;

b) reconstructing a velocity image from the acquired velocity image data;

c) calculating the rigid body motion of the organ using data acquired with the magnetic resonance imaging system;

d) producing the image indicative of organ deformation by subtracting the rigid body motion from the velocity image.

2. The method as recited in claim 1 which includes:

acquiring image data of the organ with the magnetic resonance imaging system and using the image data to reconstruct a magnitude image of the organ;

producing a mask from the magnitude image which is indicative of the organ's spatial extent; and combining the mask with the velocity image to remove from the velocity image structures which are not said organ.

3. The method as recited in claim 1 in which the velocity encoding gradient in the pulse sequence is directed along two, orthogonal, in-plane axes; and the velocity image depicts motion in an image plane through the organ.

4. The method as recited in claim 3 in which the velocity image includes two components indicative of velocity along the respective two axes, and the rigid body motion is calculated from the two velocity components.

5. The method as recited in claim 1 in which the rigid body motion is comprised of a calculated translational motion component indicative of the bulk translational motion of the organ, and a calculated rotational motion component indicative of the bulk rotational motion of the organ about an axis.

6. The method as recited in claim 1 in which the organ is a human heart and the velocity image is indicative of the velocity in a plane through a left ventricle of the heart.

7. The method as recited in claim 6 in which the pulse sequence is performed during a succession of cardiac cycles and at a selected cardiac phase during each of said cardiac cycles.

8. A magnetic resonance imaging system for producing a deformation image of a moving organ, the combination comprising:

a) means for producing a polarizing magnetic field throughout the moving organ;

b) means for producing transverse magnetization in spins located throughout the organ;

c) means for acquiring NMR signals produced by transverse magnetized spins in the organ;

d) means for producing magnetic field gradients throughout the moving organ;

e) a pulse sequencer for operating elements b), c) and d) to perform a pulse sequence that employs a velocity encoding gradient;

f) a receiver for acquiring velocity encoded NMR signals produced by transversely magnetized spins in the moving organ when the pulse sequence is performed;

g) velocity image reconstruction means responsive to the acquired velocity encoded NMR signals for producing an image indicative of spin motion in the moving organ;

h) rigid body calculation means for analyzing the image indicative of spin motion and producing information indicative of rigid body motion of the moving organ; and i) means for producing an image indicative of organ deformation by subtracting the information indicative of rigid body motion from the image indicative of spin motion.

9. The magnetic resonance imaging system as recited in claim 8 in which the rigid body calculation means includes:

means for calculating a translational motion component indicative of the bulk translational motion of the moving organ; and means for calculating a rotational motion component indicative of the bulk rotational motion of the moving organ about an axis.

10. The magnetic resonance imaging system as recited in claim 8 in which the moving organ is a human heart and the system includes:

means for producing a gating signal for the pulse sequencer such that the pulse sequence is performed at substantially one phase of the heart's cardiac cycle during acquisition of the velocity encoded NMR signals during successive heart cycles.

11. The magnetic resonance imaging system as recited in claim 8 in which the means for producing transverse magnetization is operated by the pulse sequencer to produce transverse magnetization in a slice of spins through the moving organ, the slice defining an image plane.

12. The magnetic resonance imaging system as recited in claim 11 in which the velocity encoding gradient is produced by element d) and is directed along two, orthogonal axes disposed in the image plane.

* * * * *